(12) United States Patent
Creighton, IV et al.

(10) Patent No.: US 6,459,924 B1
(45) Date of Patent: Oct. 1, 2002

(54) ARTICULATED MAGNETIC GUIDANCE SYSTEMS AND DEVICES AND METHODS FOR USING SAME FOR MAGNETICALLY-ASSISTED SURGERY

(75) Inventors: Francis M. Creighton, IV, St. Louis, MO (US); Peter R. Werp, Los Gatos, CA (US); Rogers C. Ritter, Charlottesville, VA (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/189,633

(22) Filed: Nov. 10, 1998

Related U.S. Application Data (60) Provisional application No. 60/065,105, filed on Nov. 12, 1997.

(51) Int. Cl.[7] ............................................. A61B 6/00
(52) U.S. Cl. ........................................ 600/427; 128/899
(58) Field of Search ................................ 600/427, 114, 600/424; 128/899; 248/324

(56) References Cited

U.S. PATENT DOCUMENTS

| | | | |
|---|---|---|---|
| 3,043,309 A | * 7/1962 | McCarthy | 128/899 |
| 3,358,676 A | * 12/1967 | Frei et al. | 128/899 |
| 4,244,362 A | 1/1981 | Anderson | |
| 4,809,713 A | 3/1989 | Grayzel | |
| 5,353,807 A | 10/1994 | DeMarco | |
| 5,681,260 A | 10/1997 | Ueda et al. | |
| 5,758,667 A | 6/1998 | Slettenmark | |
| 5,779,694 A | * 7/1998 | Howard et al. | 604/891.1 |
| 5,843,153 A | * 12/1998 | Johnston et al. | 607/122 |
| 6,014,580 A | * 1/2000 | Blume et al. | 600/424 |
| 6,015,414 A | * 1/2000 | Werp et al. | 606/108 |
| 6,241,671 B1 | * 6/2001 | Ritter et al. | 600/427 |

FOREIGN PATENT DOCUMENTS

FR     2252107     * 7/1975

OTHER PUBLICATIONS

McNeil et al, "Characteristics of an Improved Magnetic–Implant Guidance System", IEEE Trans. on Biomedical Engr., vol. 42, No. 8, Aug. 1995.*

Quate et al, "Goniometric Motion Controller for the Superconducting Coil in a Magnetic Stereotaxis System", IEE Trans. on Biomedical Engr., vol. 38, No. 9, Sep. 1991.*

(List continued on next page.)

*Primary Examiner*—John A. Jeffery
(74) *Attorney, Agent, or Firm*—Harness, Dickey & Pierce, P.L.C.

(57) ABSTRACT

An articulated magnet assembly optionally includes one or two additional fixed magnets to guide or move such as by pulling or pushing a magnetic structure in the body. The magnetic structure may be a magnetic tip of a catheter or a magnetic seed, or other such magnetic assembly, implant or device. The device is arranged to facilitate biplanar, real-time, X-ray imaging of the patient. The moved magnet can be a large, strong permanent magnet or a cored solenoid. The added, fixed electromagnets may have either normally conducting or superconducting coils. The magnet on the articulated magnet assembly can move radially, along a polar direction, and at an azimuthal angle, and may also pivot in place to direct an opposite pole of the magnet in the direction of the patient. Magnetically-assisted surgery can be performed, in some instances, by pivoting the magnet on one or two axes without withdrawing it from the vicinity of the patient to control the direction and/or orientation of a temporarily or permanently implanted magnetic surgical device. If the magnet is an electromagnetic coil, this pivoting may or may not have to be accompanied by a ramping of current in the coil.

8 Claims, 10 Drawing Sheets

OTHER PUBLICATIONS

Yam, Phillip, "Magnet on the Brain", Scientific American, pp. 32, Aug. 1996.*

Grady, M.S. et al, Nonlinear Magnetic Stereotaxis: Three–Dimensional, In Vivo Remote Magnetic Manipulation of a Small Object in Canine Brain, Med. Phys. 17(3), pp. 405–415, May/Jun 1990.*

Manwaring, K.H. et al, "Magnetic Field Guided Endoscopic Dissection Through a Burr Hole May Avoid More Invasive Cranitomies", Acta Neurochir, Supp, 61:34–39, 1994.*

Gaston, A., et al, "External Magnetic Guidance of Endovascular Catheters With a Superconducting Magnet: Prelim. Trials", J. Neuroradiol., 15: 137–147, 1988.*

Montgomery, D.B., et al, "A Magnetically Guided Catheter System for Intracranial Use in Man", IEEE Trans. on Magnetics, vol. 6, No. 2, p. 374–5, Jun. 1970.*

* cited by examiner

ARTICULATED MAGNETIC GUIDANCE SYSTEMS AND DEVICES AND METHODS FOR USING SAME FOR MAGNETICALLY-ASSISTED SURGERY

CROSS REFERENCE TO RELATED APPLICATION

This application claims the benefit of U.S. Provisional Application No. 60/065,105, filed Nov. 12, 1997, entitled "Articulated Magnetic Guidance System."

BACKGROUND OF THE INVENTION

1. Field of the Invention

This invention relates to a device for guiding or pulling magnetic implants in the body, and more specifically such devices and methods that provide and/or utilize an articulated, guided magnet assembly.

2. Discussion of the Prior Art

Magnetic stereotaxis systems are known in the art. One such system is disclosed in McNeil et. al., "Functional Design Features and Initial Performance Characteristics of a Magnetic-Implant Guidance System for Stereotactic Neurosurgery," IEEE Trans. on Biomed. Engrg. 42 793 (1995). The system described in this publication is a specialized application of multi-coil magnetic actuators. Other systems for magnetic surgery include those in which manually manipulated solenoids are moved about the body, such as the magnetic stereotaxis system described in Gilles et al., "Magnetic Manipulation Instrumentation for Medical Physic Research," Rev. Sci. Instrum. 65 533 (1994). The aforementioned two articles are hereby incorporated by reference in their entirety.

The systems described in the prior art have the disadvantage in that hand-held magnets are not coordinated with imaging in a precise way and cannot apply field or force gradients accurately in needed directions. Also, it has been difficult or impossible, from a practical standpoint, to apply strong magnetic fields to provide guidance or force deep within a body. Furthermore, the magnetic stereotaxis system and other similar systems with multi-coil arrangements require the solution of magnetic field equations with those solutions are not being easy to find or once found are ill-behaved. Therefore, it would be an advance in the art to provide a magnetic surgical system in which equations having simpler and more well behaved field solutions could be expected, and that is also capable of providing a strong magnetic field deep in a patient's body in a manner coordinated with an imaging device.

SUMMARY OF THE INVENTION

It is therefore an object of the invention to provide a surgical system that provides precise imaging in combination with accurate application of magnetic fields and/or force gradients in required directions for moving or guiding a magnetic implant.

It is a further object of the invention to provide a surgical system that provides precise imaging in combination with an accurately applied magnetic field, including magnetic fields stronger than are possible with hand-held magnets.

It is yet another object of the invention to provide a surgical system and method for providing precise imaging in combination with a magnetic field that can provide guidance or force deeper within the body than is practical with hand-held magnets, and in some instances far deeper.

It is still another object of the invention to provide an improved magnetic guidance system that can provide a combined guiding field and force-applying field gradient in the same desired direction through use of an articulated magnet, such fields to be used for guiding, and possibly motivating, a magnetic structure or device such as a magnetic seed or magnet of a catheter.

It is yet another object of the invention to provide an improved magnetic guidance, and possibly motive force, system that can be controlled with increased simplicity relative to prior art magnetic guidance systems.

It is yet an additional object of the invention to provide a robotically controlled magnetic system to locate an electromagnetic coil in a manner in which simpler and possibly more effective, including simpler and more well behaved, field solutions can be achieved in guiding magnetic surgical devices such as magnetic seeds and the magnetic tips of catheters.

It is still another object of the invention to provide a robotically controlled magnet system to locate a permanent magnet or magnets in a manner in which more effective field solutions can be achieved in guiding and motivating magnetic surgical implants.

These and other objects are achieved by the various embodiments of the invention as exemplified in the specification and claims hereof which includes, in a first embodiment, a moveable magnet assembly configured to provide a magnetic field in a patient when the magnet assembly is operated; and an imaging system configured to provide an image of a magnetic implant in the patient. Preferably, a bed or other support is provided for the patient. The magnet assembly is preferably robotically controlled, and may comprise either a permanent magnet or an electromagnet that is brought into the proximity of the patient. The electromagnet may be either a normally conducting electromagnet (i.e., one having resistive conductor coils) or a superconducting electromagnet. The moveable magnet assembly may comprise a track and gimbal support having radial and/or rotational motion components, as well as translational components. The imaging system may comprise two medical image display screens such as x-ray display screens, a first of which is mounted below the bed and a second of which is mounted horizontally and above the bed at a side of the bed, and further comprising two imaging tubes such as x-ray cameras, a first of which is mounted above the bed opposite the first x-ray display screen, and a second of which is mounted above the bed on a side of the bed opposite the second x-ray display screen. Alternately (or in addition thereto), a portion of the imaging system may reside on and be configured to move with the moveable magnet assembly.

In accordance with another significant aspect of the invention that is noteworthy both individually and in conjunction with the other aspects of the invention, it has been discovered that significant magnetic fields in all directions and at all locations in an operating region, into which a patient's body part desired to be operated on may be placed, such as a brain, may be achieved by pure rotation. This advantage is achieved by a magnet design in which a ratio of side magnetic field to axial magnetic field magnitude is large, as explained in more detail below.

While a brief explanation of the invention has been given, a fuller understanding of the invention may be attained by referring to the drawings and description of the preferred embodiments which follow.

BRIEF DESCRIPTION OF THE DRAWINGS

The figures are not necessarily drawn to scale.

DESCRIPTION OF THE PREFERRED EMBODIMENTS

Figure 6:
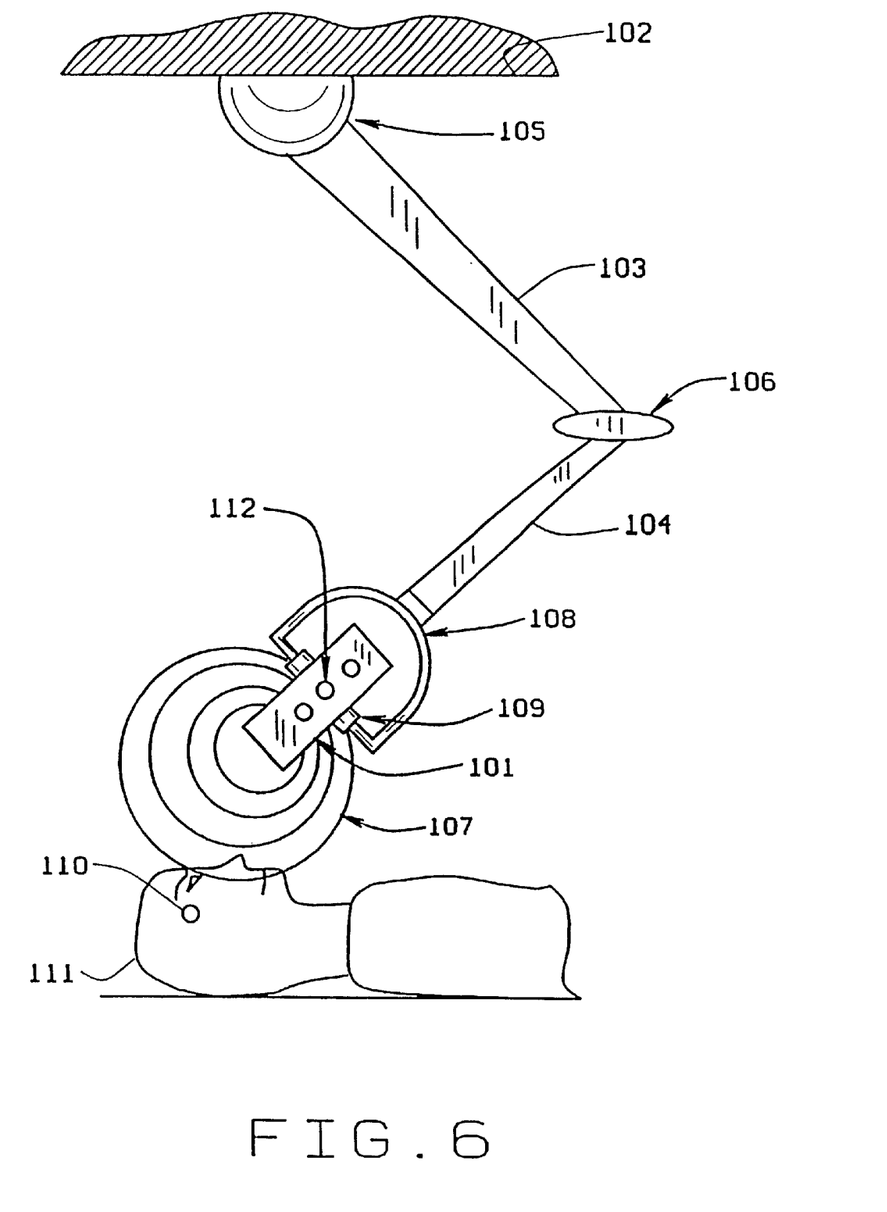
FIG. 6 is a drawing of a ceiling mounted embodiment of a permanent magnet on an arm that may be articulated either manually or by computer control.
Figure 10:
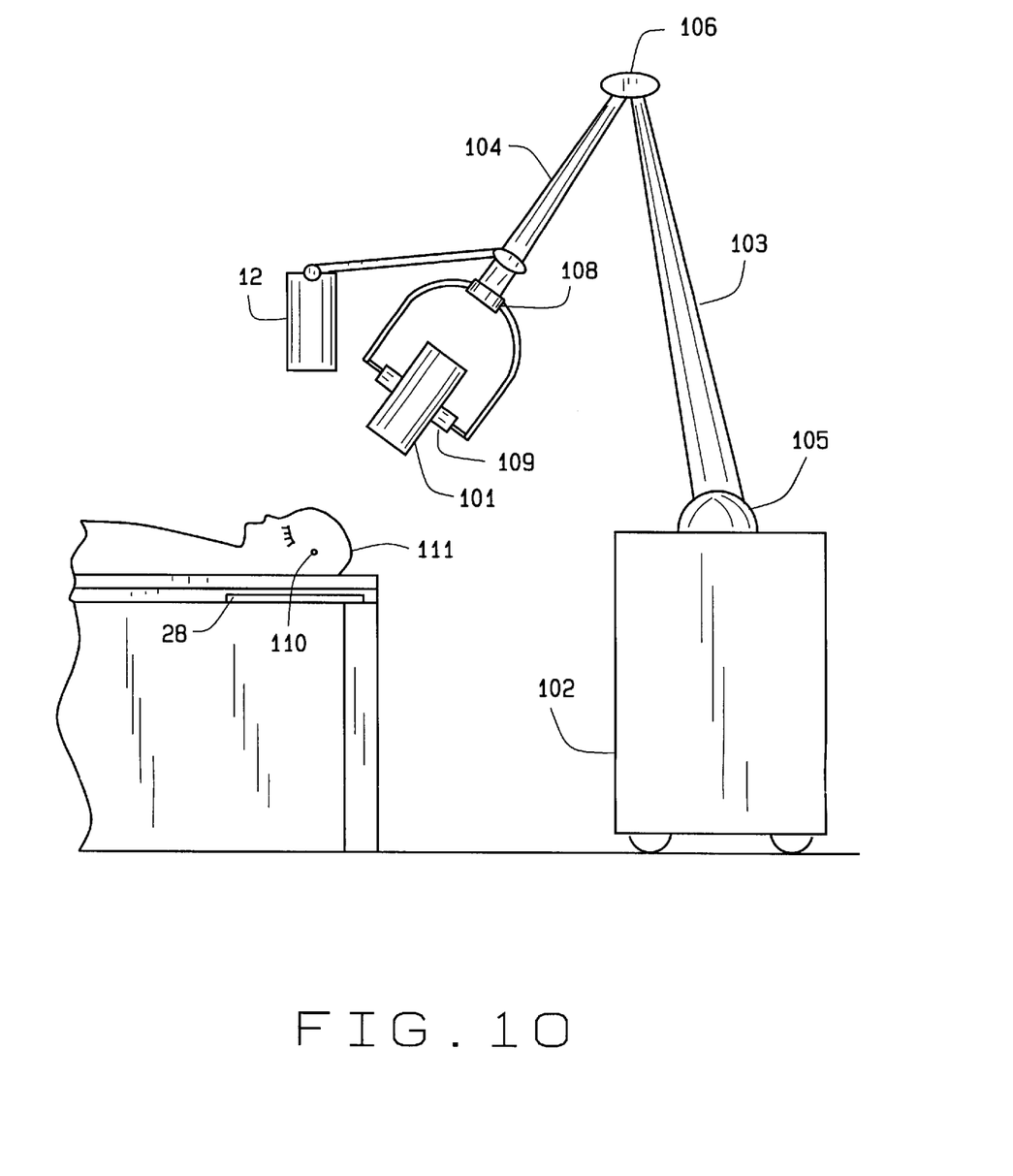
FIG. 10 is a drawing of a dolly-mounted embodiment of a permanent magnet on an arm that may be articulated either manually or by computer control.

FIG. 6 is a drawing of an embodiment of an articulation apparatus in accordance with the present invention. This apparatus employs a magnet 101 which is preferably a permanent magnet. This apparatus is similar to, but is stronger than and is an extended version of a type of articulated arm such as one that holds a dentist's drill. The illustrated embodiment shows a universal hinge 105 mounting a section 103 of the arm to a base 102 such as a ceiling, although the arm could be mounted elsewhere, for example, to a support dolly on the floor, as shown in FIG. 10. An opposite end of arm section 103 is connected to another arm section 104 by another hinge 106. Two sections of the arm 103, 104 are hinged at two points 105 and 106 to allow adjustable placement of magnet 101. This movement provides magnetic field lines 107 in a patient 111 for guidance and/or motivating such as by pulling (the latter by the gradient of the magnetic field) of magnetic surgery device or implant 110 within patient 111. For purposes of describing the present invention, the term "directing" may include either or both of guiding (navigating) and motivating such as by pushing or pulling. Pivots 108 and 109 allow magnet 101 to be rotated to provide all angles of navigation and motivation. A locating device 112 may be provided, e.g., at or near magnet 101, to aid in and keep track of the positioning of magnet 101. While this embodiment has been described as employing a permanent magnet 101, it is also possible for it to be appropriately modified to use an electromagnet, as would be apparent to one of ordinary skill in the art. It would also be apparent to one of ordinary skill in the art that an imaging device might also be supported and positioned in tandem with the magnet, or along side thereof, as shown in FIG. 10.

Figure 1:
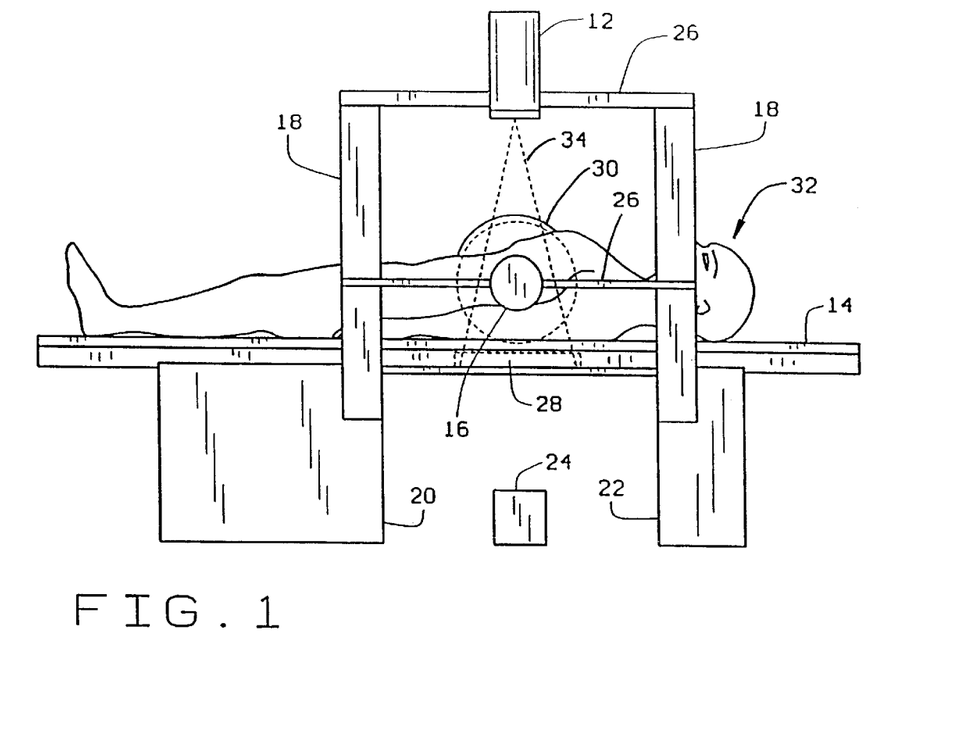
FIG. 1 is a side view of a preferred embodiment of a portion of an apparatus in accordance with the invention.

A side view of another embodiment of a portion of an apparatus in accordance with the invention is shown in FIG. 1. The apparatus includes a first X-ray source 12 located above a bed 14, a second x-ray source 16 located above and to one side of bed 14, a pair of axial magnets 18, and a bed articulating system 20 and 22. The axial magnets 18 are optional, but are included in the preferred embodiment to provide magnetic fields along the direction of the body axis where some types of moving magnets (not shown, but to be described below) cannot provide such fields. Axial magnets may comprise normally conducting or superconducting coils. The bed articulating system is shown in two parts 20 and 22 because an articulation point 24 is located between the two parts 20 and 22. Articulation point 24 is a location at which an articulated magnet pivot may rest. The articulation magnet pivot is not shown in FIG. 1, however. X-ray sources 12 and 16 are supported by support struts 26 or any other suitable structure so that they project their beams at imaging plates 28 and 30, respectively, crossing through a location above the bed where a region of interest of a patient 32 would be positioned (operating region) during an operation. A magnetic seed or other magnetically guided surgical or medicinal-carrying implement would be either temporarily or permanently implanted (implant) as a magnetic structure in the body of patient 32 in the operating region, or region of interest. Imaging plates 28 and 30 are preferably of a type capable of transferring an image to a computer and of being generally unaffected by strong magnetic fields.

Figure 2:
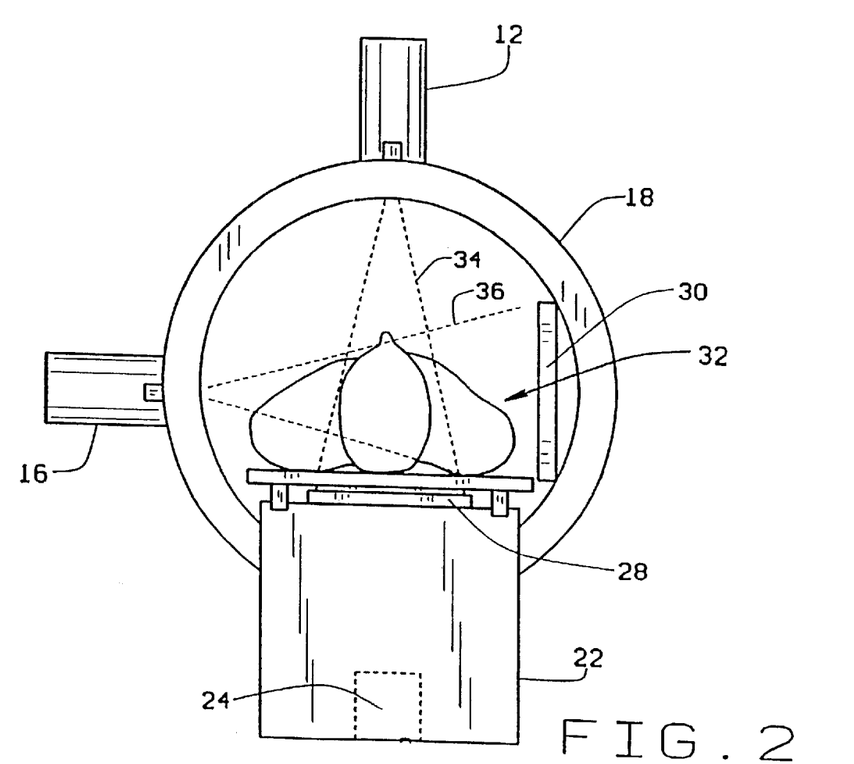
FIG. 2 is an axial view of the apparatus of FIG. 1.

A view of the apparatus of FIG. 1 from another perspective is provided by FIG. 2, which shows the apparatus as it might appear if one were positioned to the right of the head of patient 32 in FIG. 1 while looking at the apparatus. FIG. 2 more clearly shows the intersection of X-ray beams 34 and 36 in a region of interest of the body of patient 32 (operating region).

The bed articulation system 20 and 22, whether designed in two parts (as shown here), or in one or three or more parts, is designed to move bed 14 at least along a longitudinal axis, and may also be designed to move vertically, laterally, or otherwise. However, it is contemplated that motion of the bed 14, while desirable, is not necessary to the operation of the invention, which is instead more generally concerned with the articulation of a magnet in a region around patient 32.

Figure 3A:
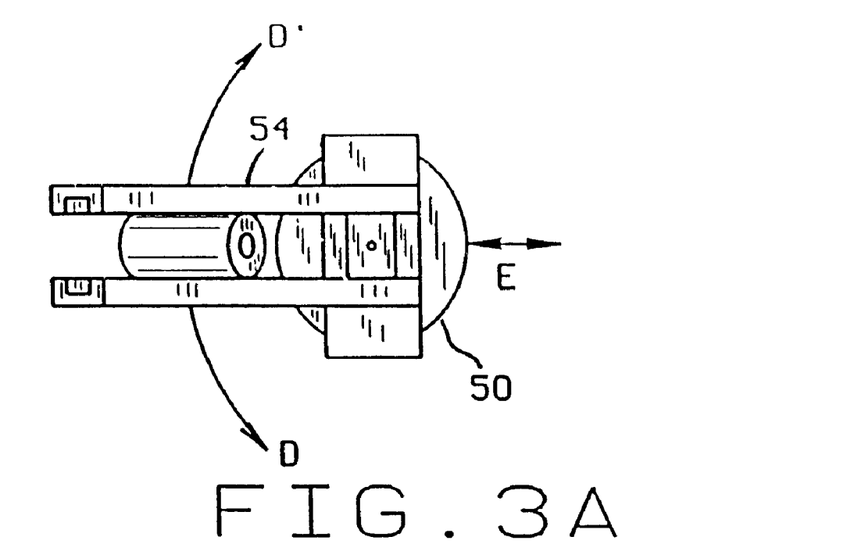
FIGS. 3A and 3B are a side and top view of an articulation apparatus for use with the apparatus of FIGS. 1 and 2.
Figure 3B:
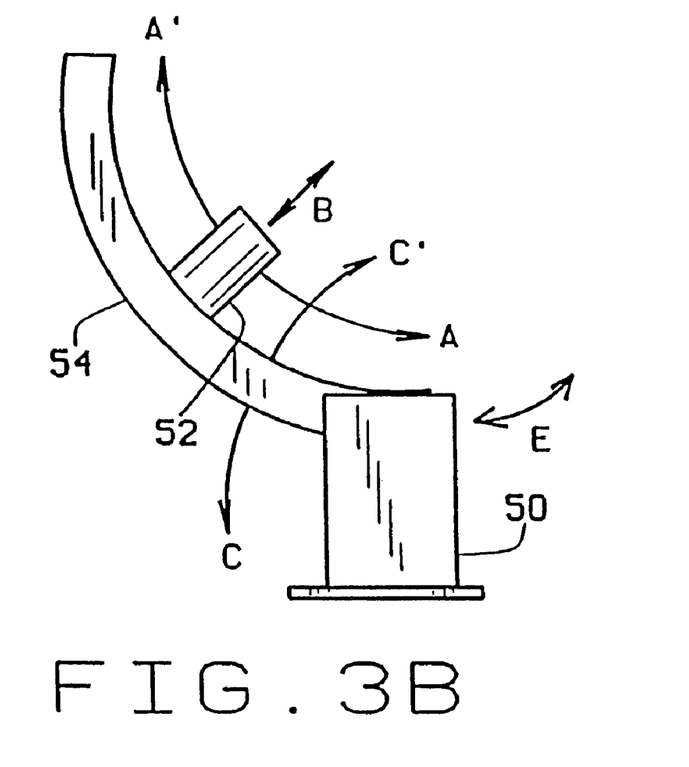

Articulation point 24 in FIGS. 1 and 2 represents a position in which a coil or magnet articulation system may be mounted in accordance with this invention. One type of articulation system suitable for use in this invention is shown in FIGS. 3A and 3B. The type of articulation system shown here is suitable for surgical procedures requiring a magnetic field only with fixed vision, i.e., the X-ray system comprising projection tubes 12, 16 and screens 28, 30 in FIGS. 1 and 2 do not move. FIG. 3A shows an articulation support 50, which may be provided in the position shown in FIGS. 1 and 2 at articulation point 24. The articulation support is provided with servo control mechanisms (not shown) to provide movement of a coil or permanent magnet 52 along an arcuate arm 54 along a polar angle A–A' and radially as indicated by arrow B. Motion of the entire arm 54 may optionally be provided by pivoting arm 54 in a direction C–C', although this motion is not required. FIG. 3B shows a top view of the apparatus shown in FIG. 3A, showing that arm 54 sweeps along an azimuthal angle, limited by the placement of axial coils 18 (shown in FIGS. 1 and 2). The apparatus as shown provides coverage of a lower portion of either the right or the left side of a patient 32 (not shown in FIGS. 3A and 3B). Arm 54 may preferably comprise a track and gimbal assembly, for example, although other arms may be used as would be apparent to one of ordinary skill in the art.

A second articulation apparatus 50, 52, 54 may be provided to provide coverage of the other side. Alternately, variations of the apparatus shown in FIGS. 3A and 3B are possible in which arm 54 provides more than 90° of polar motion for magnet 52. For example, arm 54 may itself cover an angle greater than 90° so that magnet 52 can move around the entire left or right side of patient 32. Alternately, arm 54 may itself be made moveable through articulation support 50, so that it moves in an arcuate direction indicated by arrow E in FIGS. 3A and 3B. Such motion allows for complete coverage of the back of patient 32. Combinations of these variations are also possible. As with the embodiment shown in FIGS. 3A and 3B, arm 54 may preferably comprise a track and gimbal assembly.

Figure 4:
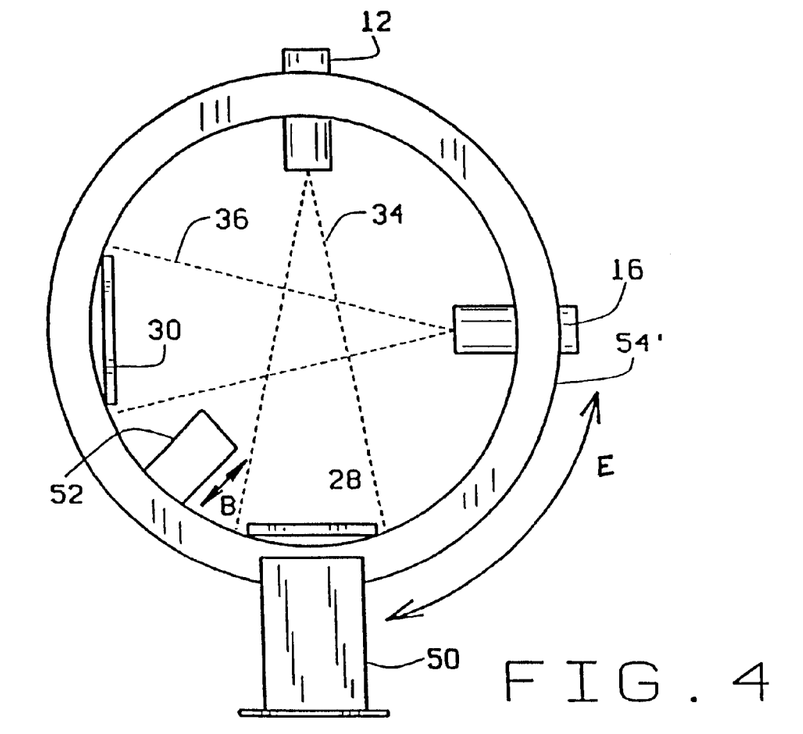
FIG. 4. is a view of an alternate coil or magnet articulation apparatus for procedures requiring force with mobile vision.

An alternate embodiment of a magnet articulation system is shown in FIG. 4. Magnet or coil 52 is mounted on a ring support 54' which, in this embodiment, also carries X-ray projectors 12 and 16, as well as imaging plates 28 and 30. The entire ring is supported by articulation support 50 so that it can be moved, preferably under control of a servo control system, in a polar angle indicated by arrow E. Although not illustrated, the ring can also be moved in an azimuthal direction similar to that shown in FIG. 3B. Magnet 52 can also move radially as indicated by arrow B in FIG. 4. Of course, if this embodiment is used, struts 26 would be omitted from the bed and axial magnet assembly of FIGS. 1 and 2, and the imaging plate 28 would not be attached to bed 14 but rather would be free to rotate around it. Variations of this embodiment are also possible, in that either X-ray tube 12, 16 and its corresponding imaging plate 28, 30 could be fixedly attached to a bed and axial magnet assembly rather than to the magnet articulation assembly shown in FIG. 4, or any of the elements shown mounted to ring 54' could be separately moveable around ring 54' without ring 54' being moved.

Figure 5A:
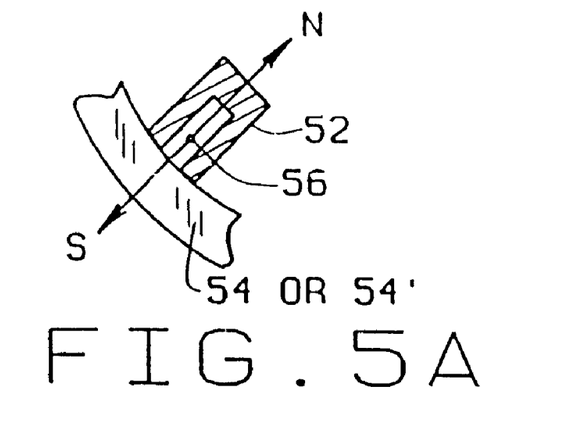
FIGS. 5A, 5B, and 5C are a sequence of illustrations of a permanent magnet pivoting at a location on an arm of the apparatus of FIGS. 3A and 3B, or on a ring of the apparatus of FIG. 4.
Figure 5B:
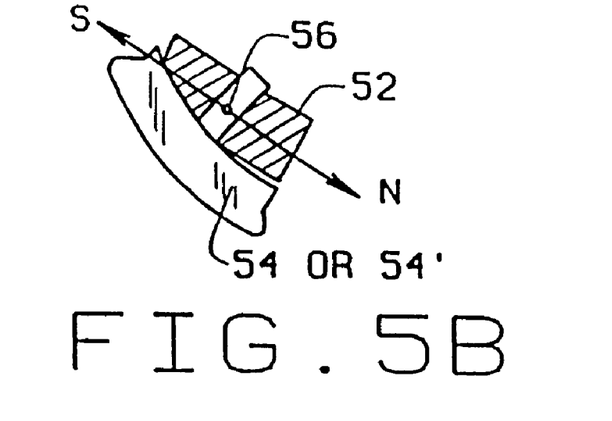
Figure 5C:
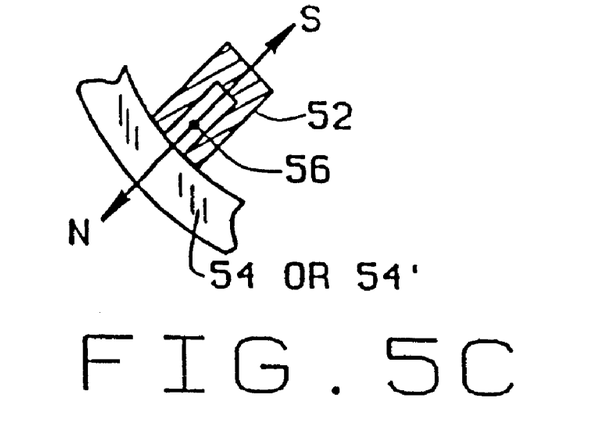

In case magnet or coil 52 comprises a permanent magnet, it is preferable to provide a pivot so that magnetic poles can be rotated to supply a magnetic field in any necessary direction during a surgical procedure. This pivoting is illustrated by the rotation of magnet 52 in the sequence of FIGS. 5A, 5B, and 5C about a pivot 56 attached to ring 54 (or 54'). The north and south poles of the magnet are shown. If this pivoting action is allowed during a surgical procedure, the magnet 52 should preferably be retracted either through a retraction motion as indicated in arrow B in FIGS. 3A and 4, or the support arm 54 should preferably be pivoted downward, away from the patient along arrow C in FIG. 3A. Alternately, a magnetic shield (not shown) of a suitable material may simply be interposed between magnet 52 and the patient to prevent the magnetic field of the rotating magnet from adversely affecting the motion of a magnet seed implanted in the patient.

Other embodiments of systems allowing coil or magnet articulation are possible. For example, a robotic arm assembly may be used. Robotic arm manipulation is standard in many industries. Examples of robotic arm manipulation may be found in U.S. Pat. No. 5,321,353 issued Jun. 14, 1994 to D. Furness, entitled "System and Method for Precisely Positioning a Robotic Arm," U.S. Pat. No. 5,086,401 issued Feb. 4, 1992 to E. Glassman, et al., entitled "Image-directed Robotic System for Precise Robotic Surgery Including Redundant Consistency Checking," U.S. Pat. No. 4,569,627 issued Feb. 11, 1986 to S. Simunovic, entitled "Robotic Manipulator," U.S. Pat. No. 4,990,839 issued Feb. 5, 1991 to W. Schonlau, entitled "Modular Robotic System," U.S. Pat. No. 5,078,140 issued Jan. 7, 1992 to Y. Kwoh entitled "Image Device-Aided Robotic Stereotaxis System," U.S. Pat. No. 5,572,999 issued Nov. 12, 1996 to J. Funda et al., entitled "Robotic System for Positioning a Surgical Instrument Relative to a Patient's Body," and U.S. Pat. No. 5,354,314 issued Oct. 11, 1994 to Hardy et al., entitled "Three-Dimensional Beam Localization Apparatus and Microscope for Stereotactic Diagnoses or Surgery Mounted on Robotic Type Arm." The disclosures of the above-identified patents are hereby incorporated in their entirety as fully as if they had been set forth herein. It is, of course, desirable that the robotic arm be provided with areas of exclusion to prevent the effector (i.e., the magnet 52) or any other part of the robot arm from accidentally coming into contact with either patient 32 or medical personnel.

Regardless of the type of coil or magnet articulation structure is provided, it is preferable that the articulation be computer-controlled, so that simpler and possibly more effective field solutions may be achieved. In particular, by providing a limited number of magnets (e.g., only the moving magnet 52 or the moving magnet in conjunction with either one or two axial magnets 18), far simpler field solutions are possible and sufficient than is the case with a larger plurality of magnets, each of which is controlled separately or in conjunction with another in pairs. Moreover, a controlling apparatus such as a computer (not shown) may be provided and coupled to articulation systems 20, 22, the pair of axial coils 18, the articulation and rotation systems illustrated in FIGS. 3A, 3B, 4, 5A, 5B, and 5C (or the alternate robotic arm assembly), as well as the imaging system 12, 16, 28, 30, as well as control current in a coil used as magnet 52. This computer control would allow for close coordination of magnetic surgery with concurrent imaging. This aspect of the invention makes it particularly useful for surgery in sensitive areas of a patient's body such as the brain.

Figure 7:
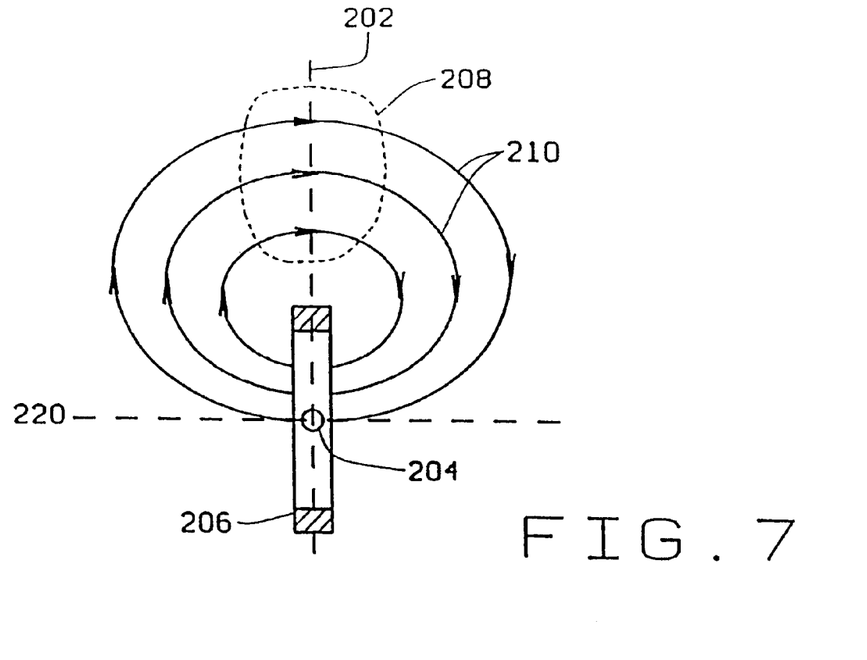
FIG. 7 is a drawing illustrating a relationship between the magnetic field lines of a preferred embodiment of an electromagnetic coil and an operating region of a patient, when the electromagnetic coil is in a first orientation.

Significant fields in all directions and all locations in an operating region of a patent, such as a brain, may be achieved by pure rotations of a magnet. Referring to FIG. 7, which is a drawing illustrating a relationship between the magnetic field lines of a preferred embodiment of an electromagnetic coil and an operating region of a patient, when the electromagnetic coil is in a first orientation, axes 202 and 204 of electromagnetic coil 206 are diagrammatically shown relative to an operating region 208. The operating region, may, for example, be a patient's brain, but could be another part of the body. Axis 204 is shown as a point, because it represents an axis perpendicular to the plane depicted in FIG. 7, which view is shown looking down on a patient. A third axis 220 perpendicular to the other two is an axis of symmetry of the coil, i.e., the axis about which the turns of the coil are wound. In observing the magnetic field lines 210 of magnet 206, it will be seen that simple rotations of magnet coil 206 about axes 202 and 204, at appropriate angles and in appropriate orders, will provide magnet field lines 210 with any desired components in the plane of FIG. 7 and perpendicular to that plane, in the operating region 208.

Rotation about axis 202 will provide field line components that can be represented as going into, or emerging from, the plane represented by FIG. 7, depending upon whether the desired "spot" (i.e., the location at which the magnetic field having the desired direction is to be provided) is to the left or to the right of axis 202, and on the direction of rotation about axis 202.

Rotation about axis 204 can shift field line directions from left to right, or the reverse, and often with a relatively small angle of rotation (i.e., as compared to 180°). This economy of rotation, i.e. sensitivity, is better illustrated by reference to FIG. 8, which is a drawing showing the relationship of the magnetic field lines of FIG. 7 to the operating region when the electromagnetic coil is rotated along an axis. In a rotation θ of 60.6° of the coil from a horizontal alignment of axis 202, field lines 210 in the operating region 208 of the patient's brain have been shifted from vertical to 4.2° from horizontal. Also shown in FIG. 8 are lines 230 representing equal magnetic field magnitude.

Figure 8:
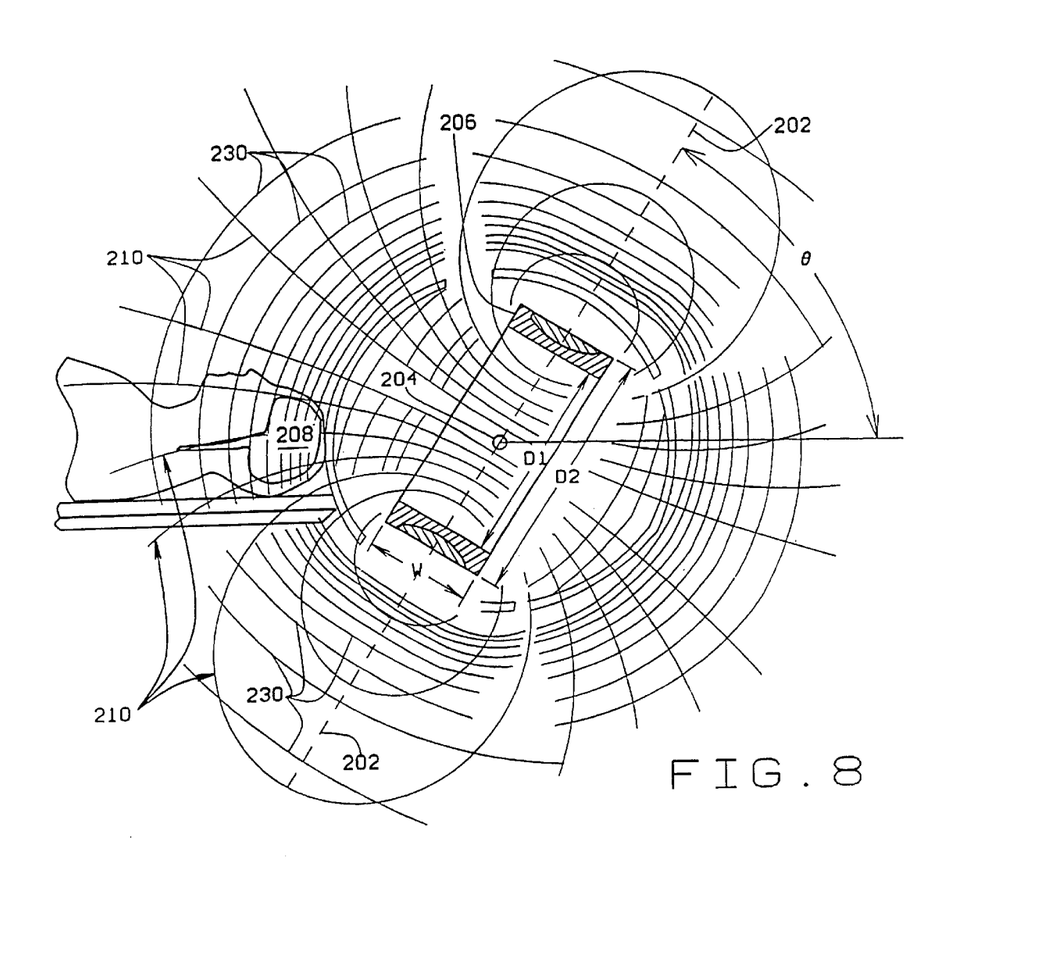
FIG. 8 is a drawing showing the relationship of the magnetic field lines of FIG. 7 to the operating region when the electromagnetic coil is rotated along an axis.

In a preferred embodiment of magnet 206, its inner coil diameter D1 as indicated in FIG. 8 is 16 inches, while its outer coil diameter D2 is 20 inches. The coil width W in the axial direction is 8 inches. (As noted above, the figures are not necessarily drawn to scale.) With these dimensions, when coil 206 is a superconducting coil with 20,000 A/cm$^2$, it can create approximately 0.4 Tesla or greater at any region of procedure in an operating region 208 of a patient's brain.

An advantage of this navigational/motivational system and method is that significant magnetic fields in all directions at all locations in a brain or other body part positioned within an operating region can be obtained merely by rotation of a magnet, without other translational movement. Preferably, a ratio of a side field (i.e., the 90° off-axis magnetic field magnitude) to an axial field is large, so that not as much power is wasted in having to drive a desired minimum field at all angles of orientation. Maintaining such field ratios decreases coil size and cost, and can make manipulation of the magnet easier. For the coil dimensions given here, axial field magnitude is about 1.4 times the side field magnitude at most distances.

While the magnet coil 206 dimensions given above have been optimized for some conditions, coils of somewhat different dimensions and shapes can be optimized differently for different magnetically-guided surgical applications.

It will be seen from the symmetry of the field lines of the coil that both or either of the side fields and the axial fields, at various times during a surgical procedure, will provide the necessary directed fields, and that reversal of field direction can be achieved by rotation about an appropriate axis, without other translational movement. It will also be seen that it is possible to change direction of the field lines in several different ways. To guide, and perhaps motivate an implanted magnetically-guided surgical device in living tissue after it is implanted, the magnet is brought into the vicinity of the operating region in which the surgical device is implanted. The magnetic field lines, or the gradient of the magnetic field, is used either to move or at least direct the motion of the surgical device. Changes in the direction of the magnetic field lines or of the gradient are made to provide changes in the direction and/or orientation of the surgical device. In some cases, a pure rotation in the dihedral plane of an intended turn can be accomplished without changing the coil current, with proper control of the axes of rotation of the coil. In some cases it will be necessary either to ramp the current to zero or down to a low magnitude before executing the rotations of the coil and then bring the current back to a desired value. In still another method, the magnet can be moved translationally away from the patient, rotated, and then brought back into position, with or without altering currents. It will be understood that similar movements of a permanent magnet may be used to direct and perhaps motivate the surgical device, although the steps involving changes in coil current would no longer be applicable in this case.

Figure 9A:
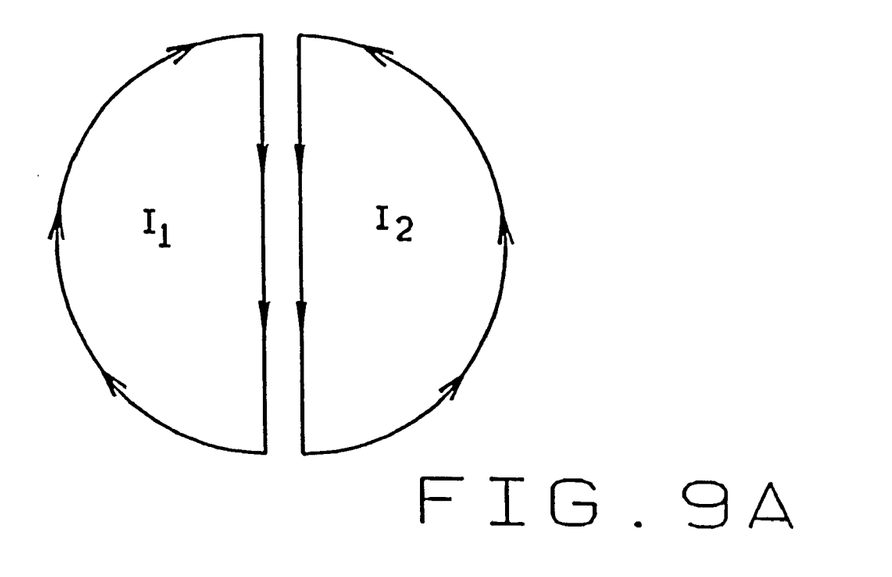
FIGS. 9A and 9B depict the plane of the windings of a pair of coils, or a split coil, in another embodiment of the invention.
Figure 9B:
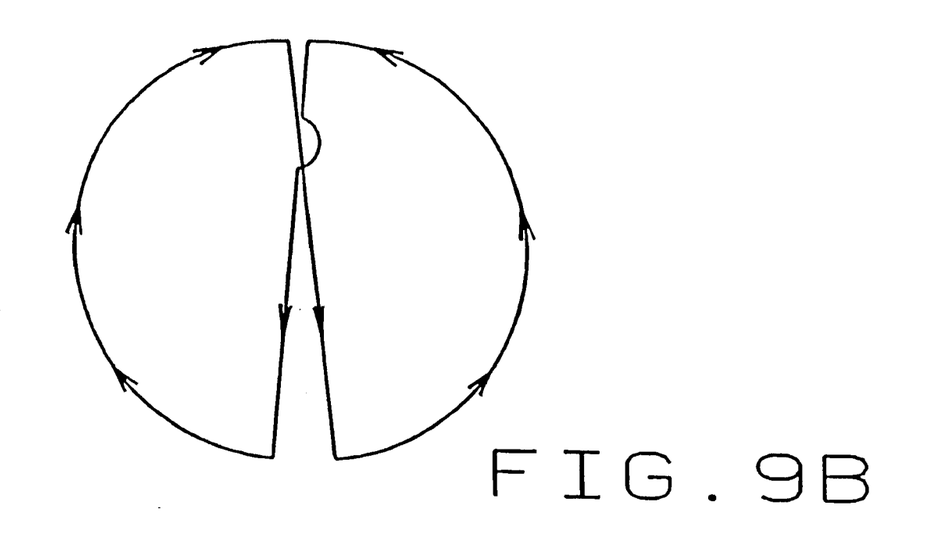

Still another embodiment of the invention, which may actually be used in the other several embodiments of the invention, comprises an articulated magnet, which may be either a pair of permanent magnets, or an electromagnet having current relationships as shown in FIGS. 9A and 9B. As shown in FIGS. 9A and 9B for the electromagnet embodiment, the plane of the windings of such a coil, or two coils, each shaped in the approximate form of a semi-circle, is energized by currents flowing in opposite senses. This same field may be created with a single coil having its two halves twisted, as shown. In the other form of this embodiment, two permanent magnets are placed side by side to make a single magnet assembly with a north and south pole facing the operating region. Alternately, the field directly in front of the magnet is parallel to the magnet face, while the fields closer to the magnet edges are perpendicular to the magnet face. Thus, a rotation of the magnet about its short axis, plus a lateral translation provides all possible magnetic field orientations in the operating region.

The magnets employed, whether permanent magnets (such as two permanent magnets side-by-side with opposite polarities) or electromagnets (such as shown in FIGS. 9A and 9B), preferably provide a quadrupole magnetic field, which is preferred because the resulting distribution of field lines is particularly suited to controlling the application of magnetic field by articulation.

The invention has been explained in the context of its preferred embodiments. One of ordinary skill in the art could readily think of alternatives and modifications to the invention, all of which are considered to be part of the invention. Furthermore, embodiments incorporating some, but not all, of the inventive features disclosed herein will provide an advantage over prior art devices and methods while achieving some, but perhaps not all, of the objects of the invention. Nevertheless, such advantageous embodiments are still considered as being encompassed within the scope of the invention. The invention should therefore be considered as being limited only by the scope of the claims appended hereto and their legal equivalents, in view of the description in the specification and drawings.

What is claimed is:

1. A device for directing a magnetic structure in living tissue positioned within an operating region, comprising:
    an articulated arm having one end mounted on a base and a second end; and
    a magnet, comprising a pair of oppositely oriented permanent magnets, pivotably mounted at the second end of the articulated arm, wherein the magnet is pivotable about each of at least two mutually perpendicular axes of the magnet to provide, in any location in the operating region, varying directions of at least one of magnetic field lines and magnetic gradient in said operating region.

2. A method of directing a magnetic structure within living tissue located within an operating region, comprising the steps of:
    embedding a magnetic structure in the living tissue;
    positioning an electromagnet to provide an effective magnetic field in the operating region;
    pivoting the magnet on at least one of at least two axes of the magnet as desired to change at least one of either the direction of movement or orientation of the magnetic structure;
    ramping a magnitude of current in the electromagnet down to a low value between the positioning and the pivoting steps, and
    ramping a magnitude of current in the electromagnet up to a selected value after moving the magnet.

3. The method of claim 2 and further comprising the step of withdrawing the magnet from the vicinity of the operating region between the positioning and pivoting steps, and repositioning the magnet to provide an effective magnetic field in the operating region after the pivoting step.

4. A device for directing a magnetic structure in living tissue positioned within an operating region, the device comprising:

(a) a magnet assembly comprising at least two permanent magnets sufficient to generate two magnetic fields of opposite polarities, and configured to rotate about at least two of its axes to provide a magnetic field in said operating region; and (b) a magnet support assembly, said magnet support assembly being controllably, mechanically re-positionable about the operating region to thereby desirably change either or both of the magnetic field strength and direction to thereby direct the magnetic structure.

5. A method of directing a magnetic structure within living tissue located within an operating region, comprising the steps of:

embedding a magnetic structure in the living tissue;

positioning an electromagnet to provide an effective magnetic field in the operating region;

moving the electromagnet as desired to change at least one of either the direction of movement or orientation of the magnetic structure;

ramping a magnitude of current in the electromagnet down to a low value between the positioning step and a pivoting step; and ramping a magnitude of current in the electromagnet up to a selected value after moving the magnet.

6. A method of directing a magnetic structure within living tissue located within an operating region, comprising the steps of:

embedding a magnetic structure in the living tissue;

positioning a magnet to provide an effective magnetic field in the operating region;

pivoting the magnet as desired to change at least one of either the direction of movement or orientation of the magnetic structure;

withdrawing the magnet from the vicinity of the operating region between the positioning step and the pivoting step; and repositioning the magnet to provide an effective magnetic field in the operating region after the pivoting step.

7. A device for directing a magnetic structure in living tissue positioned within an operating region, the device comprising:

(a) a magnet assembly comprising a magnet means sufficient to generate a quadrupole magnetic field and configured to rotate about at least two of its axes to provide a magnetic field in said operating region; and (b) a magnet support assembly, said magnet support assembly being controllably, mechanically re-positionable about the operating region to thereby desirably change either or both of the magnetic field strength and direction to thereby direct the magnetic structure.

8. A method of directing a magnetic structure within living tissue located within an operating region, comprising the steps of:

embedding a magnetic structure in the living tissue;

positioning a magnet to provide an effective magnetic field in the operating region;

pivoting the magnet on at least one of at least two axes of the magnet as desired to change at least one of either the direction of movement or orientation of the magnetic structure; and withdrawing the magnet from the vicinity of the operating region between the positioning and pivoting steps, and repositioning the magnet to provide an effective magnetic field in the operating region after the pivoting step.

* * * * *